(12) United States Patent
Somani (10) Patent No.: US 7,431,459 B2
(45) Date of Patent: Oct. 7, 2008

(54) SLIT LAMP FOR OPHTHALMIC USE

(75) Inventor: Seema Somani, Milpitas, CA (US)

(73) Assignee: Amo Manufacturing USA, LLC, Santa Ana, CA (US)

(*) Notice: Subject to any disclaimer, the term of this patent is extended or adjusted under 35 U.S.C. 154(b) by 0 days.

(21) Appl. No.: 11/969,619

(22) Filed: Jan. 4, 2008

(65) Prior Publication Data

US 2008/0106699 A1    May 8, 2008

Related U.S. Application Data

(62) Division of application No. 10/872,026, filed on Jun. 17, 2004, now Pat. No. 7,338,169.

(60) Provisional application No. 60/491,801, filed on Aug. 1, 2003.

(51) Int. Cl.
*A61B 3/10* (2006.01)

(52) U.S. Cl. ...................... 351/214; 351/221

(58) Field of Classification Search ......... 351/200–223; 359/216
See application file for complete search history.

(56) References Cited

U.S. PATENT DOCUMENTS

| | | | |
|---|---|---|---|
| 4,838,679 A | 6/1989 | Bille | 351/205 |
| 4,920,467 A | 4/1990 | Honsberger | 362/658 |
| 5,828,439 A | 10/1998 | Ueno | 351/205 |
| 5,861,939 A | 1/1999 | Heacock | 351/208 |
| 6,063,108 A | 5/2000 | Salansky | 607/89 |
| 6,183,086 B1 | 2/2001 | Neubert | 351/221 |
| 6,283,596 B1 | 9/2001 | Yoshimura et al. | 351/214 |
| 6,319,273 B1 | 11/2001 | Chen et al. | 607/88 |
| 6,357,877 B2 * | 3/2002 | Takada | 351/221 |
| 6,547,394 B2 | 4/2003 | Doherty | 351/221 |
| 7,083,281 B2 * | 8/2006 | Yogesan et al. | 351/214 |
| 2003/0053310 A1 | 3/2003 | Sommers | 361/231 |
| 2003/0058405 A1 | 3/2003 | Cornsweet et al. | 351/212 |
| 2005/0099602 A1 * | 5/2005 | Spediacci et al. | 351/214 |

* cited by examiner

*Primary Examiner*—Mohammed Hasan
(74) *Attorney, Agent, or Firm*—Townsend & Townsend & Crew LLP; Mark D. Barrish (57) ABSTRACT

A slit lamp for illuminating an eye comprises several LEDs electrically coupled to an LED driver. A user input accepts input for a length, a width and an intensity of a shaped beam of light. An LED driver selectively drives a set of LEDs of an LED array to form a shaped light beam having a desired size across a beam cross-section. In some embodiments, several optical fibers at a first end of a fiber optic manifold are optically coupled to LEDs of an LED array, and an optic is placed near a second end of a fiber optic manifold. Several ends of optical fibers of the fiber optic manifold are optically coupled to the set of selectively driven LEDs, and are arranged so as to form the shaped light beam having a desired size across the beam cross-section.

14 Claims, 6 Drawing Sheets

SLIT LAMP FOR OPHTHALMIC USE

CROSS-REFERENCES TO RELATED APPLICATIONS

This is a divisional patent application which claims priority from U.S. patent application Ser. No. 10/872,026 filed on Jun. 17, 2004, which claims the benefit under 35 USC 119(e) of U.S. Provisional Patent Application No. 60/491,801 filed Aug. 1, 2003, the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

This invention generally relates to surgical devices, systems, and methods, and more particularly to slit lamps used to illuminate and view an anterior segment of an eye during an ophthalmic examination.

Slit lamps are used in ophthalmic applications to view an anterior segment of an eye with a beam of light. The anterior segment of an eye typically comprises a cornea, an iris, a sclera, an anterior lens capsule, a posterior lens capsule, and/or a lens nucleus. A beam of light is generated by the slit lamp to illuminate these tissues while a user views the illuminated area, often through a magnification optic such as a microscope. The beam of light can have a varying beam cross-section. For example, the beam of light will often be focused to form a narrow slit. Such a beam is desirable for examining layers of a cornea of an eye. In other instances, for example when viewing a large area of an eye, the user adjusts the beam to a wide beam cross-section. Slit lamps often pass light through a slot aperture. In many instances, the variation in the light beam is accomplished by mechanically changing a width across the slot aperture.

During Laser In-Situ Keratomileusis (LASIK) eye surgery, surgeons evaluate quality and positioning of a LASIK incision and resulting flap of tissue with a slit lamp. The beam of light from the slit lamp is well suited for viewing debris under a LASIK flap and also for viewing wrinkles in a LASIK flap. Debris and flap wrinkles are appropriately treated and corrected upon detection with a slit lamp examination.

While ophthalmic lamps proposed to date may be generally effective for patient examinations, further improvements would be desirable. In general, it would be desirable to provide slit lamps having decreased size and complexity. For example, slit lamps having fewer moving parts while providing a variable beam of light would be desirable.

BRIEF SUMMARY OF THE INVENTION

The present invention provides improved methods and systems for illuminating an eye during an ophthalmic examination.

In one embodiment, the invention provides a lamp for selectively illuminating a region of an eye. An LED driver selectively drives a first set of a plurality of LEDs so as to generate a shaped light beam illuminating the eye with a first size across a cross-section of the beam. An input is coupled to a driver, and the driver drives a second set of the LEDs in response to a signal from the input so as to illuminate the eye with a second beam cross-section. A second cross-sectional size is different than a first cross-sectional size.

In some embodiments, the first cross-sectional size is related to a first size across a first set of LEDs, and the second cross-sectional size is related to a second size across a second set of LEDs. The first cross-sectional size across the first set of LEDs is different than the second cross-sectional size across the second set of LEDs, and the first set of LEDs comprises LEDs from the second set of LEDs. The first set of LEDs comprises a first number of LEDs, and the second set of LEDs comprises a second number of LEDs. The first number of LEDs is different than the second number of LEDs.

In specific embodiments, the first cross-sectional size is greater than the second cross-sectional size and the first number of LEDs is greater than the second number of LEDs. The first set of LEDs emits a first amount of light energy and the second set of LEDs emits a second amount of light energy. The first amount of light energy is greater than the second amount of light energy. Alternatively, the first cross-sectional size is smaller than the second cross-sectional size, and the first number of LEDs is smaller than the second number of LEDs. The first set of LEDs emits the first amount of light energy and the second set of LEDs emits the second amount of light energy. The first amount of light energy is smaller than the second amount of light energy.

In a specific embodiment, the lamp is a slit lamp, and the shaped light beam has an elongate cross-section as the light beam illuminates the eye. The signal controls a width of the shaped light beam, a length of the shaped light beam, and an intensity of the shaped light beam.

In another embodiment, the invention provides a slit lamp for illuminating an eye. The slit lamp comprises an array of LEDs. An LED driver has a first configuration driving a first set of LEDs and a second configuration driving a second set of LEDs. At least one optic directs light generated by the array toward the eye. Light from the optic comprises a beam with an elongate cross-section having a first cross-sectional size when the LED driver is in the first configuration and a second cross-sectional size when the LED driver is in the second configuration. The second cross-sectional size is different than the first cross-sectional size. The first cross-sectional size is often related to a first size across the first set of LEDs, and the second cross-sectional size is often related to a second size across the second set of LEDs. The first cross-sectional size across the first set of LEDs is different than the second cross-sectional size across the second set of LEDs.

In specific embodiments, the microscope provides a view of an anterior segment of the eye to a user while the light beam illuminates the eye. A micro-lens optic is optically coupled to the LED array. The optic is selected from the group consisting of a lens, a micro-lens array and a diffractive optic. At least one LED emits white light. The slit lamp comprises at least one monolithic array of LEDs. The array of LEDs is a hybrid array of LEDs comprising LEDs from a monolithic array of LEDs and individual LEDs. Alternatively, the array of LEDs may comprise multicolor LEDs. The LED driver drives a portion of an LED array in the second configuration and the second cross-sectional size is less than the first cross-sectional size. A user input generates a signal. The LED driver drives the portion of the LED array in response to the signal. The portion of the LED array driven by the LED driver is disposed over an area. A size across the area of the portion of the LED array driven by the LED driver corresponds to the second cross-sectional size of an elongate beam. The array of LEDs is disposed over an area, the area of the portion of LEDs driven by the LED driver is included within the area of the LED array. The area of the portion of the LED array driven by the LED driver has an elongate shape.

In specific embodiments, a fiber optic manifold comprises several optical fibers, and has a first end and a second end. Several optical fibers of the first end of the manifold are coupled to several LEDs of the LED array. The second end of the manifold emits light generated by the LED array, and optical fibers at the second end of the manifold are arranged so as to form the beam having the elongate cross-section. An optic is placed at the second end of the manifold. The optic is selected from the group consisting of a lens, a micro-lens array and a diffractive optic. Several ends of several optical fibers at the second end of the manifold are optically coupled to the portion of an LED array and disposed over an area. A size across the area corresponds to the second cross-sectional size across the elongate beam.

In another aspect, the invention provides a method of selectively illuminating a region of an eye with a shaped beam of light. Driving a first set of LEDs from a plurality of LEDs generates the shaped beam of light having a first size across a cross-section of the shaped beam. A user input generates a signal. Driving a second set of the plurality of LEDs in response to the signal from the user input generates the shaped light beam having a second size across a cross-section of the shaped beam. The second cross-sectional size is different from the first cross-sectional size.

In many embodiments, the first set of LEDs overlaps with the second set of LEDs. The signal effects a change in a number of driven LEDs. The signal from the user input can result in a reduction from the first cross-sectional size to the second cross-sectional size. The first set of LEDs can emit a first amount of light energy and the second set of LEDs can emit a second amount of light energy so that the signal provides a reduction from the first amount of light energy to the second amount of light energy. Alternatively, the first cross-sectional size can be smaller than the second cross-sectional size and the first number of LEDs can be smaller than the second number of LEDs. The first set of LEDs can emit a first amount of light energy and the second set of LEDs can emit a second amount of light energy so that the signal provides an increase from the first amount of light energy to the second amount of light energy.

In specific embodiments, a plurality of LEDs comprises several sets of LEDs. The several sets of LEDs have a different number of LEDs, each set of LEDs being selectably energized by the driver so as to provide varying beam characteristics. The second set of LEDs can comprise a number of LEDs that is less than a total number of LEDs. The plurality of LEDs comprises an array of LEDs. The shaped light beam has an elongate cross-section near the eye. The second cross-sectional size may comprise a width across the beam cross-section, and the second cross-sectional size may comprise a length across the beam cross-section. The shaped beam can be transmitted through a bundle of optical fibers.

DETAILED DESCRIPTION OF THE INVENTION

The present invention relates generally to systems and methods of illuminating an eye with light, and more specifically to systems and methods of illuminating an anterior segment of an eye with slit lamp.

Figure 1:
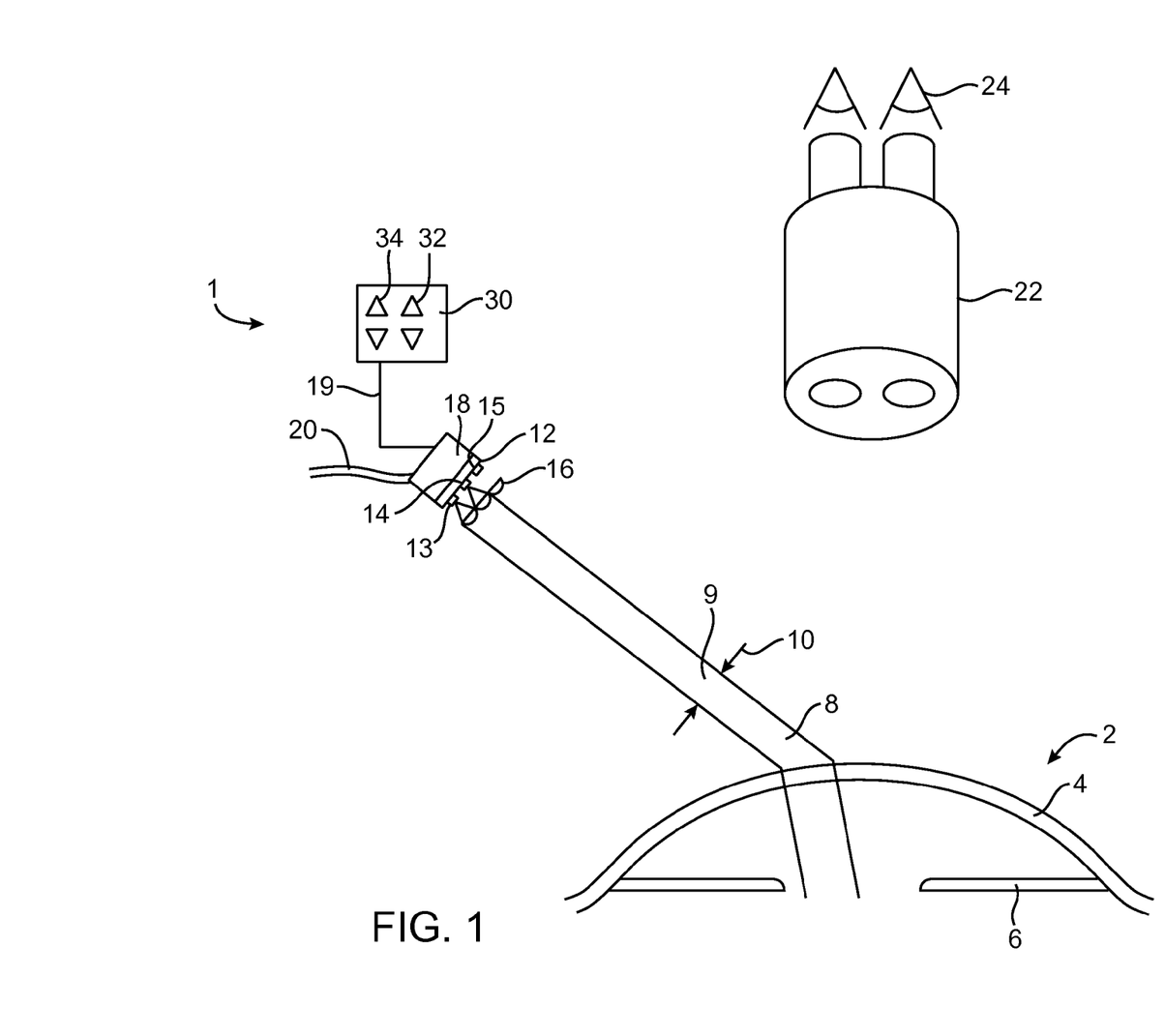
FIG. 1 illustrates a slit lamp having a shaped beam of light illuminating an eye in which a width across a shaped beam is determined by a number of LEDs used to illuminate an eye in accordance with an embodiment of the invention.

As illustrated in FIG. 1, an eye 2 having a cornea 4 and an iris 6 is illuminated with a slit lamp 1 having a shaped beam of light 8 having a cross-section 9 with a size 10 across a cross-section 9 in accordance with an embodiment of the invention. An LED array 12 is positioned near a micro-lens array 16. LED array 12 comprises a plurality of individual LEDs such as LEDs 13, 14 and 15. Micro-lens array 16 is positioned a focal length from individual LEDs to collimate light emitted from LEDs as the shaped light beam 8, which travels toward the eye 2. A portion of LED array 12 comprising LEDs 13 and 14 emits light. The size 10 across the cross-section 9 of the beam 8 is determined by a number of LEDs emitting light. An eye 24 of an operator is able to view the eye 2 through a microscope 22.

An LED driver 18 selectively drives LEDs 12, 13 and 14 of LED array 12. A user input device 30 is operationally coupled to LED driver 18 with an electrical connection 19. The user input device 30 includes a first control 32 that adjusts the size 10 across the cross-section 9 of the shaped light beam 8. The first user control 32 sends an electrical signal to the LED driver 18. The LED driver 18 selectively drives LEDs of the LED array 12 in response to a signal from the first user control 32. A second control 34 of the user input 30 adjusts an intensity of the light beam 8.

Figure 1A:
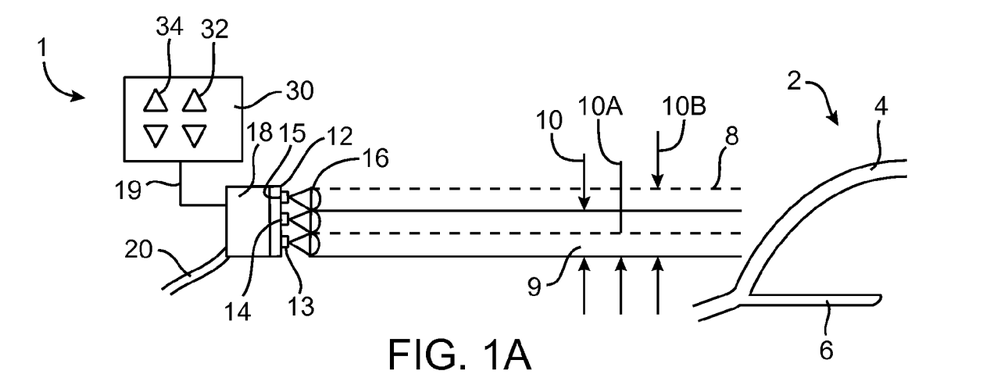
FIG. 1A. illustrates different sizes across a cross-section of a shaped beam in accordance with an embodiment of the invention.

As illustrated in FIG. 1A, the eye 2 having the cornea 4 and the iris 6 is illuminated with slit lamp 1 in accordance with the embodiment of the invention as in FIG. 1. The LED driver 18 selectively drives any combination of LEDs 13, 14 and 15 in response to a signal from control 30. In a first state the LED driver 18 drives a first set of LEDs comprising LEDs 13 and 14 so as to form the shaped light beam 8 having the size 10 across cross-section 9. A second state of LED driver 18 drives a second LED set comprising LED 13 so as to form shaped light beam 8 having a size 10A across cross-section 9. A third state of LED driver 18 drives a third set of LEDs comprising LEDs 13, 14 and 15 so as to form shaped light beam 8 having a size 10B across cross-section 9.

Figure 2:
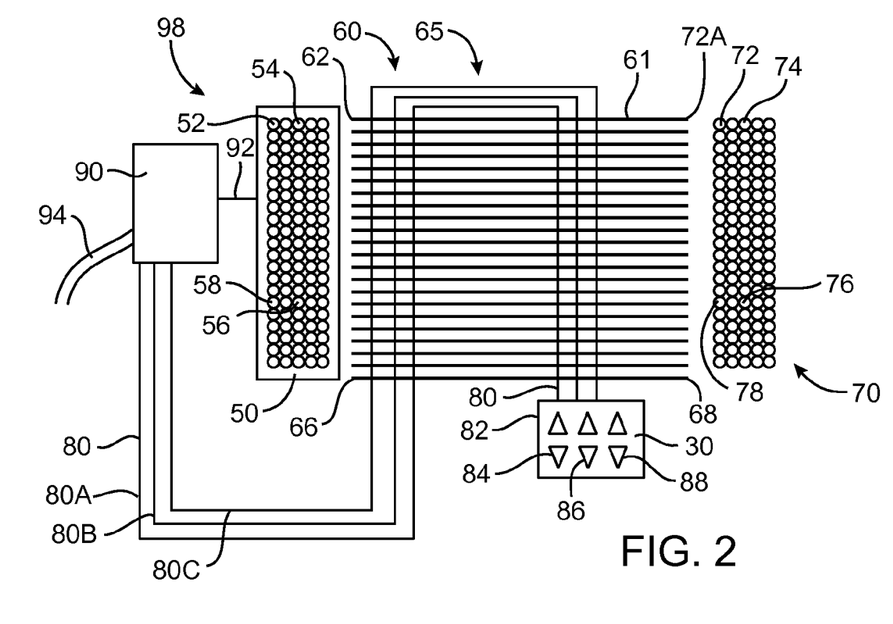
FIG. 2 illustrates a slit lamp using a fiber optic manifold to couple light energy from an LED array to a micro-lens array in accordance with an embodiment of the invention.

Referring to FIG. 2, an exemplary embodiment of a slit lamp using a two dimensional array of LEDs and having an elongate beam adjustable along two sizes of a beam cross-section is illustrated in accordance with an embodiment of the invention. An array of LEDs 50 comprises a plurality of LEDs, for example LEDs 52, 54, 56 and 58. LEDs of the array 50 are arranged in horizontal rows and vertical columns. For example LEDs 52 and 58 are disposed in the same column as LEDs 54 and 56, and LEDs 52 and 54 are disposed in the same row as LEDs 56 and 58. An individual LED of an array is expressed in matrix notation as LED (Row, Column). For example, LEDs 52, 54, 56 and 58 are expressed as LED (1,1), LED (1,3), LED (15, 3) and LED (15,1) respectively. In an alternate embodiment an LED array comprises a linear array of LEDs coupled to optical fibers. An additional embodiment comprises an array of LEDs having variable spacing between LEDs. An LED preferably emits white light. Suitable LEDs include white light LEDs having a model number LW A67C, commercially available from OSRAM Opto Semiconductors, San Jose, Calif. and Regensburg, Germany. Any LED can be used in LED array 50. For example, in some embodiments an LED array comprises a monolithic LED array commercially available as a custom order from PRP OPTOELECTRONICS of Northamptonshire, England. In some embodiments, any color of light is made by combining light from several LEDs in which each LED emits light having any one of the colors of red, blue and green. For example, white light is made by combining light from several LEDs in which each of the LEDs emits light having any one of the colors of red, blue and green.

An optical fiber manifold 60 has a first end 66 and a second end 68. Individual LEDs of the LED array 50 are optically coupled to individual optical fibers of the first end 66 of the fiber optic manifold 60. Any number of known techniques and structures can be used to optically couple an LED with an optical fiber. For example, in a preferred embodiment, light from an LED is coupled to an optical fiber using direct proximity coupling, also referred to as butt coupling. In alternate embodiments an optic is used to couple light into an optical fiber. Any optic selected from the group consisting of a single lens, a lens array and a diffractive optic can be used to couple light into an optical fiber. The optic is placed at a suitable distance from the LED so that light is optimally coupled into the optical fiber. For example, a convergence angle of an emitted cone of light and a numerical aperture of the optical fiber are matched. In a preferred embodiment, an individual optical fiber 61 of the fiber optic manifold 60 has a first end 62 and a second end 72A. Any optical fiber can be used in the fiber optic manifold 60, for example a multimode fiber model F-MBB available from NEWPORT CORPORATION, Irvine, Calif., and an InfiniCor® SXI optical fiber available from CORNING INC., Corning, N.Y.

In some embodiments, the fiber optic manifold 60 comprises an image preserving bundle of optical fibers, also referred to as a coherent bundle, such as a fiber optic bundle model number IG 163A available from Schott Fiber Optics, Southbridge Mass A suitable fiber optic bundle is commercially available as a custom order from PAGE AUTOMATED TELECOMMUNICATION, INC., Mountain View, Calif. The first end 62 of optical fiber 61 may be optically coupled to any LED, for example LED 52. The second end 68 of the fiber optic manifold 60 is optically coupled to a micro-lens array 70.

The micro-lens array 70 comprises 5 columns and 20 rows having a total number of 100 micro-lenses. The micro-lens array 70 comprises several individual micro-lenses, for example micro-lenses 72, 74, 76 and 78. A micro-lens array having a part number 0500-45-S is commercially available from ADAPTIVE OPTICS, INC. of Cambridge, Mass. Similar micro-lens arrays can be used. Preferably, each micro-lens is optically coupled to an end of an individual optical fiber so as to avoid cross talk. For example, the micro-lens 72 is optically coupled to the second end 72A of the optical fiber 61. The lenses of the micro-lens array 70 are preferably positioned a focal length away from an end of an optical fiber. Each LED is predominantly coupled to a micro-lens with a single optical fiber. For example LEDs 52, 54, 56 and 58 are optically coupled to the micro-lenses 72, 74, 76 and 78 respectively. Any number of known techniques and structures as described above can be used to optically couple optical fibers with optics at the second end 68 of the fiber optic manifold 60. For example, any optic selected from the group consisting of a single lens, a lens array, and a diffractive optic can be used. The fiber is placed at a position close to a focal length of the selected optic. In some embodiments, a mechanical aperture is placed at the second end 68 of the fiber optic manifold 60 to shape an emitted beam of light. Each micro-lens emits a beam of collimated light toward eye 2. In an alternate embodiment, a micro-lens array comprises a diffractive optical element having a repeating pattern of diffractive optical elements designed to minimize spherical aberration.

User input device 30 as described above comprises a user input control 82. The control 82 accepts input from a user. Any input device can be used as user input device 30 including keyboards, joysticks, trackballs, mice keypads, push button pads, and any input device of the VISX STAR S4™, which is commercially available from VISX, INCORPORATED of Santa Clara, Calif. A first control 84 adjusts a length of shaped light beam 8 as described above. A second control 86 adjusts a width of shaped light beam 8 as described above, and a third control 88 adjusts an intensity of shaped light beam 8 as described above. In an alternate embodiment, an additional input adjusts a color of a light beam. An LED driver 90 is operationally coupled to the user input control 82 by an electrical connection 80 comprising a plurality of wires, for example wires 80A, 80B, and 80C. The wires 80A, 80B and 80C are interwoven among several optical fibers of manifold 60 to form a single cable 65. In an embodiment, wires 80A, 80B and 80C comprise a cable separate from fiber optic manifold 60. The LED driver 90 receives signals from the user input control 82 transmitted over the electrical connection 80 comprising the wires 80A, 80B and 80C. The LED driver 90 selects a set of LEDs from the array 50 in response to signals transmitted from the user input device 30.

In an embodiment, the LED driver 90 controls each individual LED independently. By providing individual control of each LED, the width and the length of the light beam can be changed in very small increments. A minimum size of such an incremental change beam size is related to spacing between the LEDs and the optical fibers. Also, such individual control of LEDs permits any cross-sectional shape of light beam to made. For example, a set of LEDs can be selected to form a beam with a cross-section having crescent shape. Selected LEDs are driven and emit light. The intensity of light emitted from a set of selected LEDs is also adjusted by LED driver 90 in response to signals from the user input control 82. The LED driver 90 adjusts an electrical drive current passing through a selected LED. Hence, a user is able to adjust the intensity of light emitted from the set of selected LEDs. The LED driver 90 is electrically coupled to the LED array 50 with electrical wires 92. An electrical power supply cord 94 passes electrical current to the LED driver 90 and supplies the LED driver 90 with electrical energy. An LED module 98 comprises the LED array 50 and the LED driver 90.

Figure 2A:
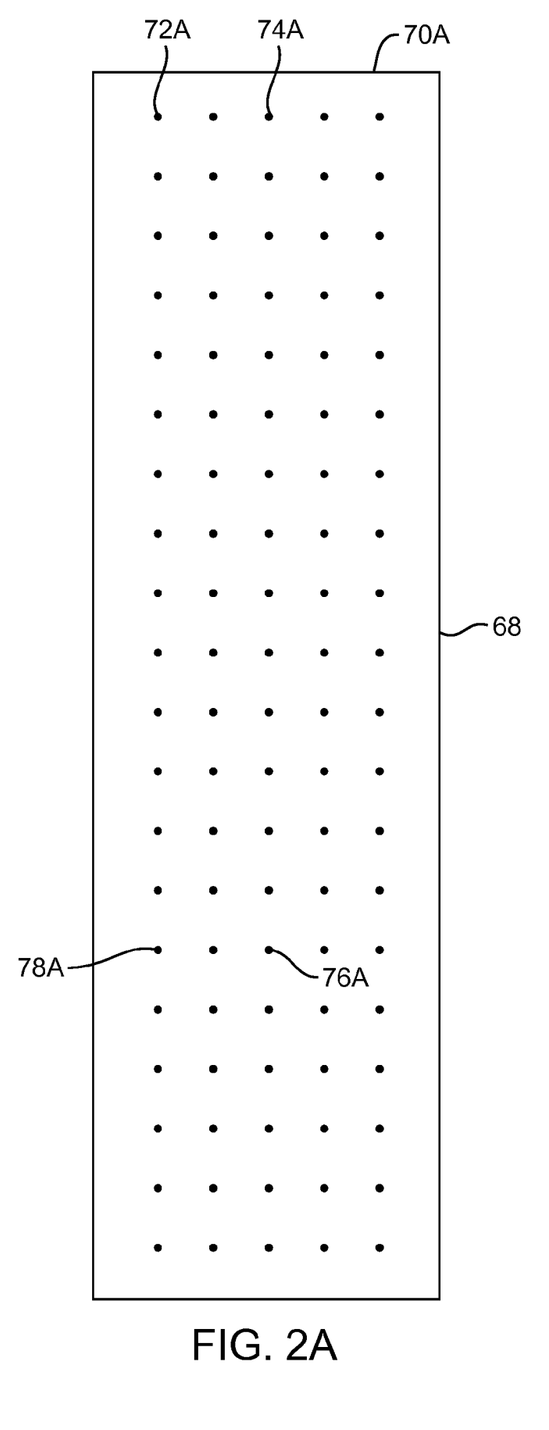
FIG. 2A illustrates a second end of a optical fiber manifold comprising an array of several ends of optical fibers disposed over an area in accordance with an embodiment of the invention

As illustrated in FIG. 2A, the second end 68 of the optical fiber manifold 60 comprises an array 70A of several ends of optical fibers disposed over an area in accordance with an embodiment of the invention. For example, the second end 72A of the optical fiber 61 and ends 74A, 76A, and 78A of additional optical fibers are disposed over a generally rectangular area of the second end 68 of the optical fiber manifold 60. The array 70A of optical fibers ends having 5 columns and 20 rows comprises a total number of 100 optical fiber ends. The optical fiber ends 72A, 74A, 76A and 78A are optically coupled to the micro-lenses 72, 74, 76 and 78A respectively.

To form a generally rectangular shaped beam of light, the LED driver selectively activates a set of LEDs comprising each LED within a rectangular area, for example an area bounded by the LEDs 52,54, 56 and 58. A first set of LEDs are optically coupled to each optical fiber end within a generally rectangular area bounded by the optical fiber ends 72A, 74A, 76A and 78A, and each diffractive optic within a generally rectangular area bounded by the micro-lenses 72, 74, 76 and 78. A portion of an array 70 optical fiber ends comprising 3 columns and 16 rows having a total number of 48 optical fibers are optically coupled to a portion of the array 50 comprising 48 LEDs disposed over a rectangular area of the LED array 50. The LED array 50 comprises 5 columns and 20 rows having a total number of 100 LEDs. A rectangular area of the LED array 50 comprising 3 columns and 16 rows is bounded on four corners by the LEDs 52, 54, 56 and 58. The LED driver 90 selects and drives LEDs within the rectangular region bounded by LEDs 52, 54, 56 and 58 to emit light from the rectangular region of the LED array 50. Light emitted from the rectangular region comprising a portion of LED array 50 is emitted from a rectangular region comprising a portion of fiber optic array 70A bounded by the optical fiber ends 72A, 74A, 76A and 78A as described above. Light from the fiber optic array 70 forms a beam of light having a rectangular cross-section.

Figure 2B:
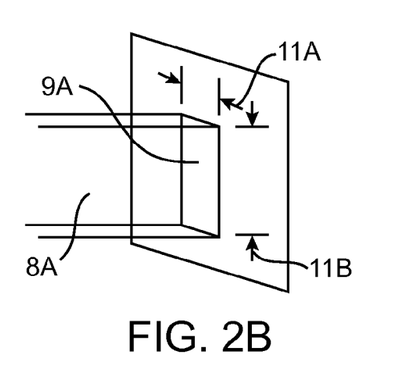
FIG. 2B illustrates a beam of light having a rectangular cross-section in accordance with an embodiment of the invention.

Referring to FIG. 2B, a beam of light 8A having a rectangular cross-section 9A is illustrated in accordance with an embodiment of the invention. Sizes across beam cross-section 9A include a width 11A across cross-section 9A and a length 11B across the cross-section 9A. Any size across a cross-section of beam 8A is determined by LEDs selectively driven by the LED driver. The width 11A across the cross-section of beam 8A is determined by a number of columns of LEDs driven by the LED driver. The length 11B across the cross-section 9A is determined by a number of rows driven by the LED driver. For example, a first set of LEDs comprising a portion of the LED array 50 is bounded by LED (1,1), LED (1,3), LED (15,3) and LED (15,1) respectively as described above. A first configuration of the LED driver driving 45 LEDs comprises the first set of LEDs so as to produce a beam having a first width 11A across the cross-section 9A and a first length 11B across the cross-section 9A. A second set of LEDs comprising a portion of the LED array 50 is bounded by LED (1,1), LED (1,2), LED (15,2) and LED (15,1). A second configuration of the LED driver driving 30 LEDs comprises the second set of LEDs so as to produce a beam having a second width 11A across the cross-section 9A and the first length 11B across cross-section 9A. The second width 11A is less than the first width 11A across cross-section 9A. A third set of LEDs comprising a portion of LED array 50 is bounded by LED (1,1), LED (1,2), LED (10,2) and LED (10,1). A third configuration of the LED diver driving 20 LEDs comprises the third set of LEDs so as to produce a beam having the second width 11A across cross-section 9A and the second length 11B across the cross-section 9A. The second length 11B is less than the first length 11B across the cross-section 9A. Any length and width can be selected with any set of LEDs.

Any LEDs of the LED array comprise a set of LEDs. For example, the following LEDs comprise a set of LEDs: LED (1,1), LED (2,2), LED (3,3), LED (4,4), LED (5,5), and LED (10,4). Several sets of LEDs exist, and a number of usable sets of LEDs exceeds a number of LEDs in the array. An amount of light energy emitted by an LED is approximately the same for each LED driven by the LED driver having similar electrical parameters, e.g. current. A subsequent amount of light energy emitted by a set of LEDs is proportional to a total number of LEDs comprised within the set. Therefore, an amount of light energy emitted by a first set of 45 LEDs is greater than an amount of light energy emitted by a second set 30 LEDs, and the amount of light energy emitted by the second set of 30 LEDs is greater than an amount of light energy emitted by a third set of 20 LEDs.

Figure 3:
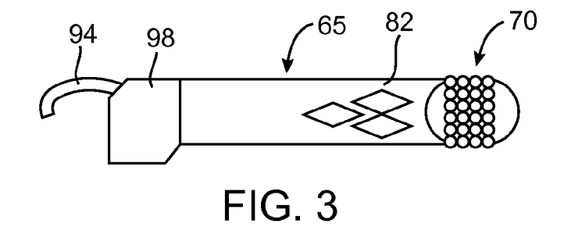
FIG. 3 illustrates a slit lamp having an elongate cylindrical shape that can be held in a hand of a user and having external controls adjustable by a user in accordance with an embodiment of the invention.

Referring to FIG. 3, a slit lamp having an elongate cylindrical shape that can be held in a hand of a user and having external controls adjustable by the user is illustrated in accordance with an embodiment of the invention. A single cable 65 comprises a fiber optic manifold and control wires as described above. The LED module 98 comprising the LED array 50 is optically coupled to the cable 65 as described above. The power supply cord 94 supplies electrical energy to the LED module 98 as described above. The user input control 82 transmits signals to the LED module 98 as described above. The micro-lens array 70 is optically coupled to the cable 65 as described above. Light emitted from the micro-lens array 70 forms the shaped beam as the light beam travels toward the eye as described above.

Figure 4:
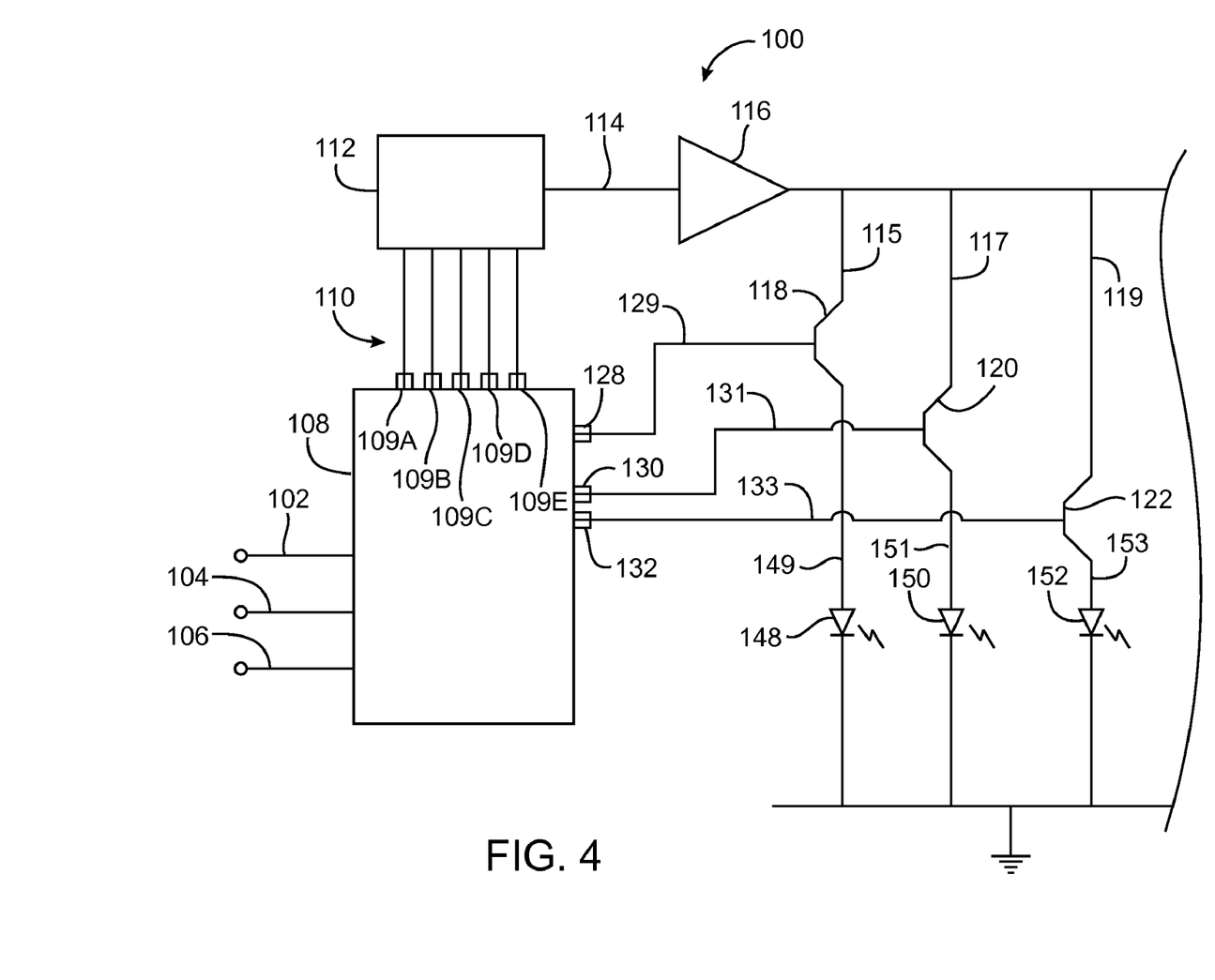
FIG. 4 illustrates an LED driver circuit for driving several LEDs in response to a user input at a control in accordance with an embodiment of the invention.

Referring to FIG. 4, an LED driver 100 having a circuit for driving several LEDs in response to a user input at a control is illustrated in accordance with an embodiment of the invention. Signals from the user input control communicated along control wires 102, 104 and 106 control the length, the width and the intensity of the shaped light beam. A gate array 108 comprises a Stratix™ EP1S10 field programmable gate array having 426 user input/output pins, and is available from ALTERA CORPORATION located in San Jose, Calif. A digital to analog converter 112 is electrically coupled to the gate array 108 with electrical wires 110 attached to output pins 109A, 109B, 109C, 109D and 109E of the gate array 108. The digital to analog converter 112 is electrically coupled to an amplifier 116 with a wire 114. The digital to analog converter 112 outputs a voltage to the amplifier 116. The amplifier 116 is electrically connected in parallel to transistors 118, 120 and 122 with wires 115, 117 and 119. The amplifier 116 applies a voltage to the transistors 118, 120 and 122. Gate array outputs 128, 130 and 132 are electrically coupled to gates of the transistors 118, 120 and 122 with wires 129, 131 and 133, respectively. LEDs 148, 150 and 152 are electrically coupled to the transistors 118, 120 and 122 respectively with the wires 149, 151 and 153. The gate array outputs 128, 130 and 132 selectively turn on the LEDs 148, 150 and 152 respectively in response to the user inputs 102 and 104. An intensity of light output by the LEDs 148, 150 and 152 is determined by a voltage applied to the transistors 118, 120 and 122. The voltage applied to the transistors 118, 120 and 122 is determined by signals from the output pins 109A-109E in response to the user input 106. The gate array 108 is programmed to selectively activate LEDs of the LED array to control the length and the width across the beam of light illuminating the eye as described above. While three LEDs are shown in FIG. 4, several hundred LEDs can be driven by additional pins of the gate array. For example, each individual LED of LED array 50 comprising 100 LEDs as described above is readily driven by the LED driver scheme illustrated in FIG. 4. Any gate array can be used to drive any number of LEDs. For example, a Stratix™ EP1S80, available from ALTERA CORPORATION, has 1,203 input output pins, and can drive over one thousand LEDs.

Figure 4A:
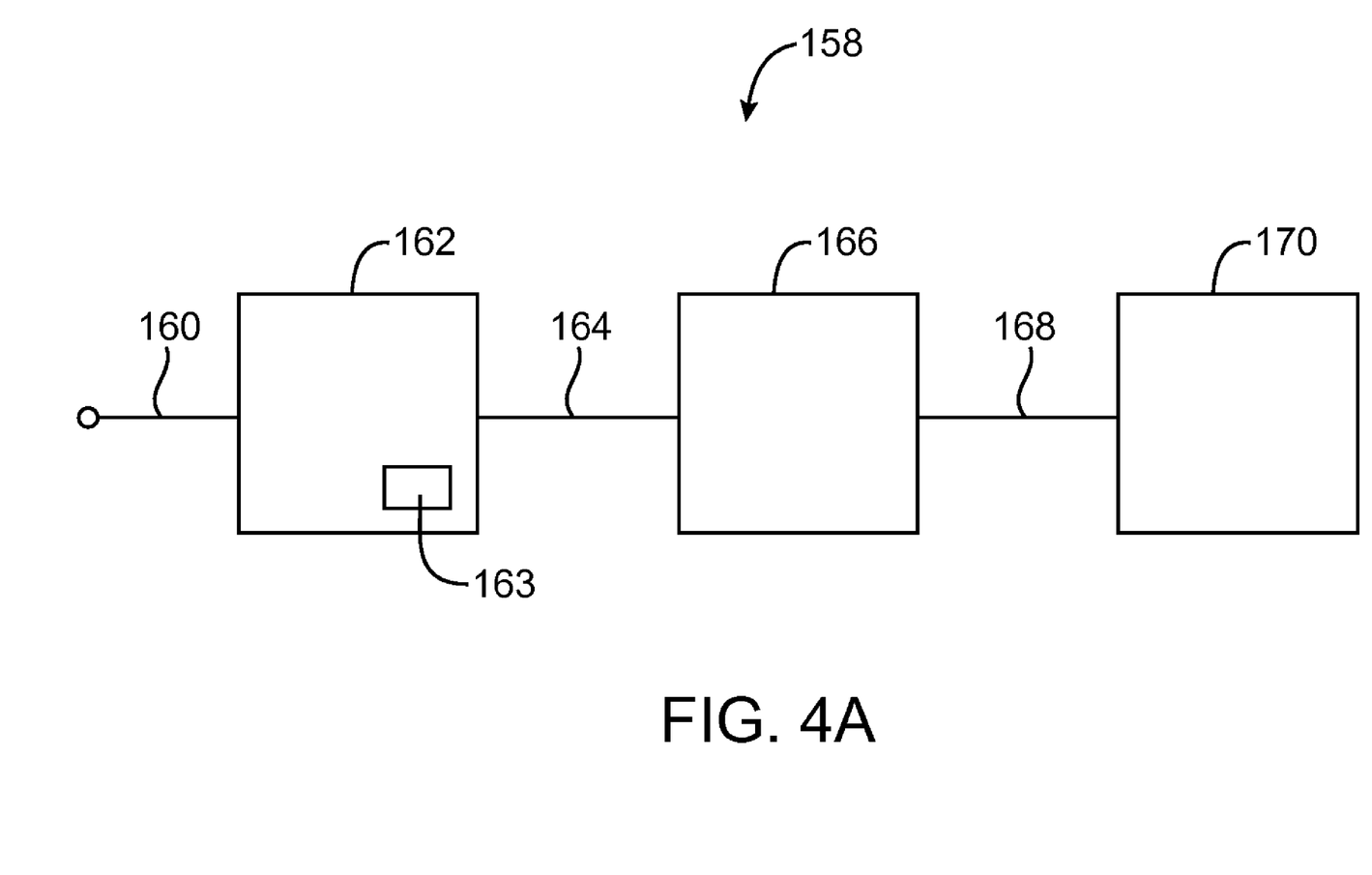
FIG. 4A illustrates an LED driver comprising a processor and display driver in accordance with an embodiment of the invention.

Referring to FIG. 4A, an LED driver 158 comprises a processor 162 and a display driver 166 in accordance with an embodiment of the invention. A cable 160 electrically connects the processor 162 to the input device as described above and passes electrical signals between the processor 162 and the input device. A processor comprises elements of a pc workstation including a central processing unit (CPU) such as an Intel Pentium processor available from INTEL CORPORATION of Santa Clara, Calif. The processor 162 comprises a tangible medium 163. The tangible medium 163 comprises any data storage medium such as a floppy disk drive, CD ROM drive and erasable programmable read only memory (EPROM). A bus 164 electrically connects the processor 162 with a display driver 166. Suitable display drivers are a MAX6953 available from MAXIM INTEGRATED PRODUCTS, INC., Sunnyvale Calif., and LM3354, LM3355 and FPD33684 display drivers available from NATIONAL SEMICONDUCTOR of Santa Clara, Calif. The display driver 166 is electrically connected to an LED array 170 using wires 168. A signal from an operator input is transmitted over the cable 160 and the processor 162 selects any set of LEDs and any intensity of driven LEDs in response. A computer program is stored on the tangible medium 163 and comprises instructions for selecting LEDs and intensities of LEDs in response to signals from an operator input device. A signal is transmitted from a computer 162 to a display driver 166 over a bus 164. The LED driver 166 drives LEDs of LED array 170 in response to signals from an operator input so as to control a shape and an intensity of a light beam as described above.

Figure 5:
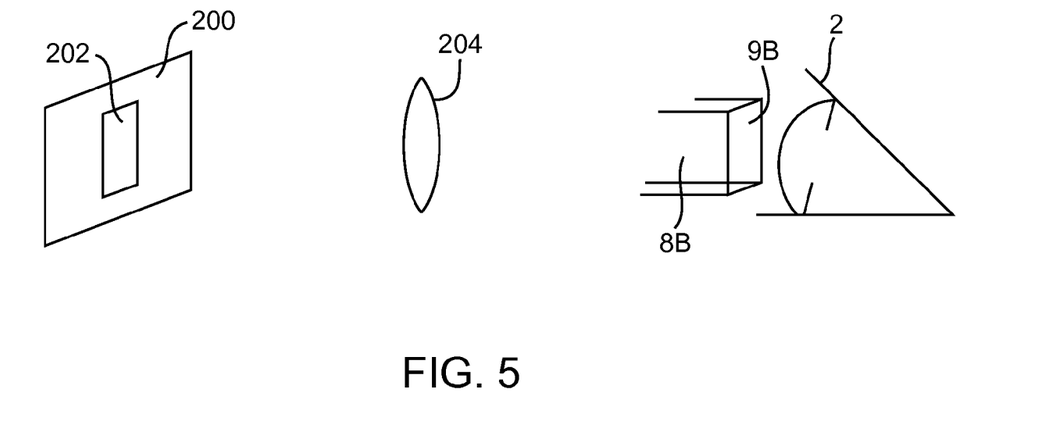
FIG. 5 illustrates a lens imaging light emitted by an LED array in accordance with an embodiment of the invention.

Referring to FIG. 5, a lens 204 imaging light emitted by an LED array 200 is illustrated in accordance with an embodiment of the invention. A set 202 of LEDs comprising a portion of the LED array 200 is disposed over an area and selected by the LED driver to emit light as described above. The Lens 204 images light emitted from LED array 200 to form a shaped light beam 8B comprising an image of the set 202 of driven LEDs near the eye 2. The light beam 8b has a rectangular cross-section 9B near eye 2. In an alternate embodiment, the lens 204 images light emitted by optical fibers disposed over an area as described above so as to from the shaped light beam having a rectangular cross-section.

While exemplary embodiments of the present invention have been described in some detail, by way of example and for clarity of understanding, a variety of changes, modifications, and adaptations will be obvious to those of skill in the art. For example, embodiments of above described slit lamp may be integrated with any operating microscope and any refractive laser surgery system, for example a Star S4™ Excimer Laser System, available from VISX, INCORPORATED of Santa Clara, Calif. Further, any light source including lasers and incandescent lights can be selected and driven with electrical power to emit light and form a shaped beam. Also, while reference has been had to rectangular beams of light, systems and methods of the present invention can be used to make a light beam having a cross-section with any shape. Hence, the scope of the present invention is limited solely by the appended claims.

What is claimed is:

1. A method of selectively illuminating a region of an eye with a shaped beam of light, the method comprising:
   driving a first set of LEDs from a plurality of LEDs to generate the shaped beam of light having a first size across a cross-section of the beam;
   generating a signal from a user input; and
   driving a second set of the plurality of LEDs in response to the signal from the user input to generate the shaped light beam having a second size across a cross-section of the beam, the second cross-sectional size being different from the first cross-sectional size.

2. The method of claim 1 wherein the first set of LEDs overlaps with the second set of LEDs.

3. The method of claim 1 wherein the signal effects a change a number of LEDs driven.

4. The method of claim 3 wherein the signal from the user input results in a reduction from the first cross-sectional size to the second cross-sectional size.

5. The method of claim 4 wherein the first set of LEDs emits a first amount of light energy and the second set of LEDs emits a second amount of light energy, so that the signal produces a reduction from the first amount of light energy to the second amount of light energy.

6. The method of claim 3 wherein the first cross-sectional size is smaller than the second cross-sectional size and the first number of LEDs is smaller than the second number of LEDs.

7. The method of claim 6 wherein the first set of LEDs emits a first amount of light energy and the second set of LEDs emits a second amount of light energy, so that the signal produces an increase from the first amount of light energy to the second amount of light energy.

8. The method of claim 1 wherein the plurality of LEDs comprises several sets of LEDs having a different number of LEDs, each set of LEDs being selectably energized by the drivers to as to provide varying beam characteristics.

9. The method of claim 1 wherein the second set of LEDs comprises a number of LEDs less than a total number of LEDs comprised within the plurality of LEDs.

10. The method of claim 1 wherein the plurality of LEDs comprises an array of LEDs.

11. The method of claim 1 wherein the shaped light beam has an elongate cross-section near the eye.

12. The method of claim 11 wherein the second cross-sectional size comprises a width across the beam cross-section.

13. The method of claim 11 wherein the second cross-sectional size comprises a length across the cross-section.

14. The method of claim 1 further comprising transmitting the shaped beam through a bundle of optical fibers.

* * * * *